United States Patent
Hall et al.

(10) Patent No.: US 10,920,408 B2
(45) Date of Patent: Feb. 16, 2021

(54) ANTIMICROBIAL TOILET WITH ELECTROLYZER

(71) Applicants: David R. Hall, Provo, UT (US); Steven J. M. Butala, Provo, UT (US); Joshua Larsen, Spanish Fork, UT (US); Jared Reynolds, Pleasant Grove, UT (US)

(72) Inventors: David R. Hall, Provo, UT (US); Steven J. M. Butala, Provo, UT (US); Joshua Larsen, Spanish Fork, UT (US); Jared Reynolds, Pleasant Grove, UT (US)

(73) Assignee: Hall Labs LLC, Provo, UT (US)

( * ) Notice: Subject to any disclaimer, the term of this patent is extended or adjusted under 35 U.S.C. 154(b) by 73 days.

(21) Appl. No.: 16/170,015

(22) Filed: Oct. 24, 2018

(65) Prior Publication Data
US 2020/0131749 A1    Apr. 30, 2020

(51) Int. Cl.
| | | |
|---|---|---|
| *E03D 9/02* | (2006.01) | |
| *A61L 2/03* | (2006.01) | |
| *C02F 1/46* | (2006.01) | |
| *C02F 1/461* | (2006.01) | |
| *C02F 1/467* | (2006.01) | |
| *C02F 103/00* | (2006.01) | |

(52) U.S. Cl.
CPC ............ *E03D 9/02* (2013.01); *A61L 2/035* (2013.01); *C02F 1/467* (2013.01); *C02F 1/46109* (2013.01); *C02F 2103/005* (2013.01); *C02F 2201/461* (2013.01); *C02F 2303/04* (2013.01); *C02F 2307/00* (2013.01); *E03D 2009/028* (2013.01)

(58) Field of Classification Search
CPC ..... E03D 9/02; E03D 2009/028; A61L 2/035; C02F 1/46109; C02F 1/467; C02F 2103/005; C02F 2201/461; C02F 2303/04; C02F 2307/00
USPC .............................................. 4/232
See application file for complete search history.

(56) References Cited

U.S. PATENT DOCUMENTS

| | | | | |
|---|---|---|---|---|
| 3,568,215 | A * | 3/1971 | Riedel | B63B 29/00 4/317 |
| 3,816,073 | A * | 6/1974 | Miller | A47K 11/02 4/302 |
| 2006/0064805 | A1* | 3/2006 | Yamamoto | E03D 9/05 4/213 |
| 2009/0127128 | A1* | 5/2009 | Kitaori | A61L 2/0088 205/464 |
| 2013/0205487 | A1* | 8/2013 | Yagi | E03D 11/13 4/420 |
| 2014/0352048 | A1* | 12/2014 | Nakamura | E03D 9/005 4/309 |

* cited by examiner

*Primary Examiner* — Janie M Loeppke

(57) ABSTRACT

The antimicrobial toilet includes one or more pairs of electrodes positioned below a water line when the hydraulic circuit is at equilibrium. The pairs of electrodes may be connected to a power source by electrical wires. In some embodiments, the electrodes are positioned on the inner wall of the toilet bowl and in some embodiments, the electrodes are positioned within the siphon tube. In some embodiments, the electrodes are metal strips and in others they are circular. When actuated, an electrical current passes through the toilet water between the electrode pairs resulting in disinfected water. Some embodiments include a pump and water conduit which transfers disinfected water to areas above the water line and emits the water to wash areas of the toilet.

18 Claims, 14 Drawing Sheets

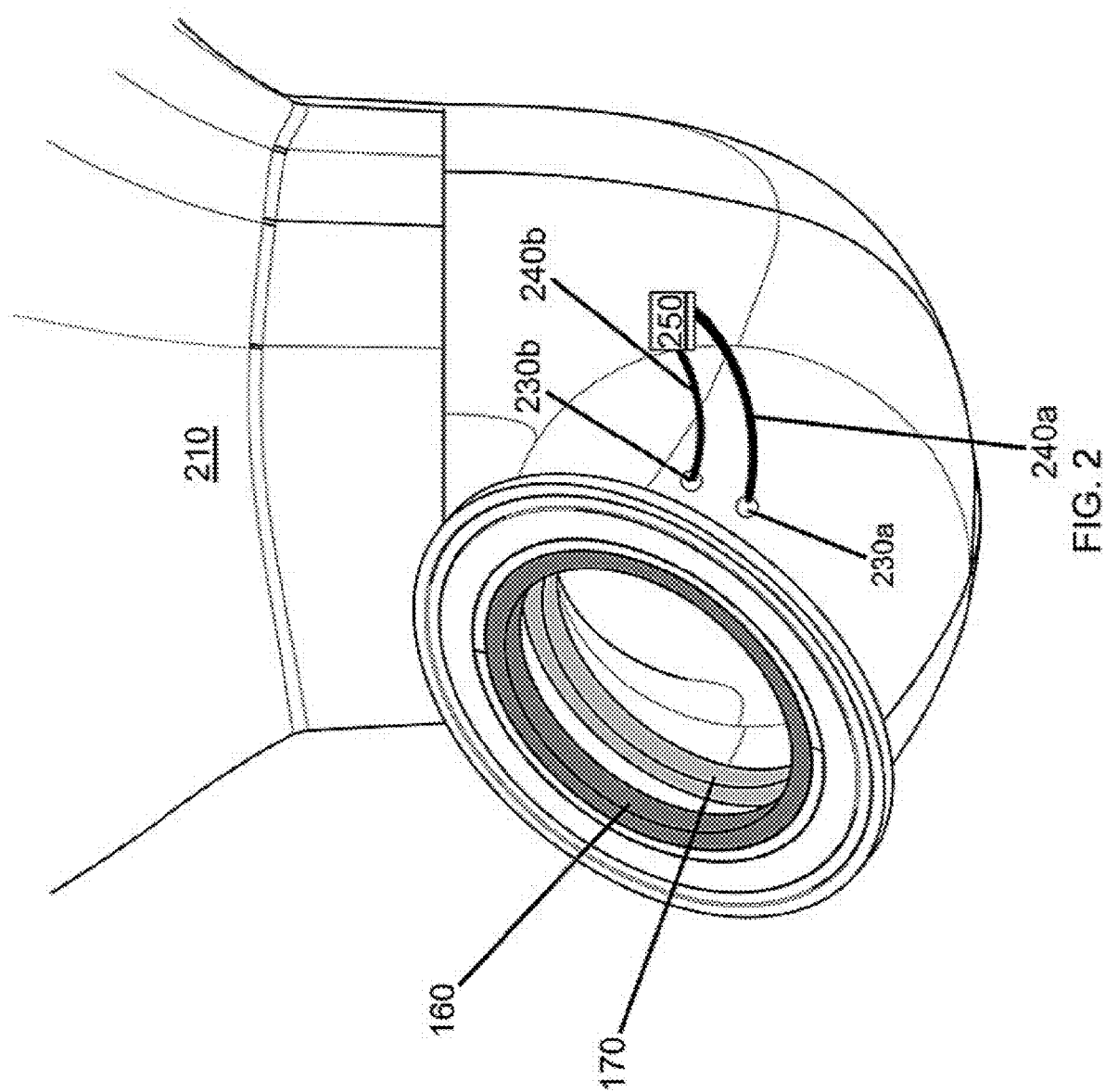

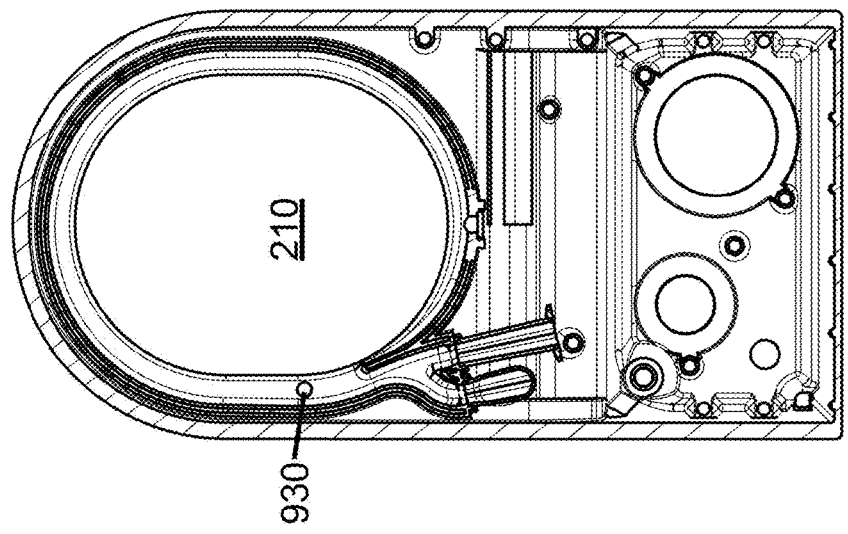
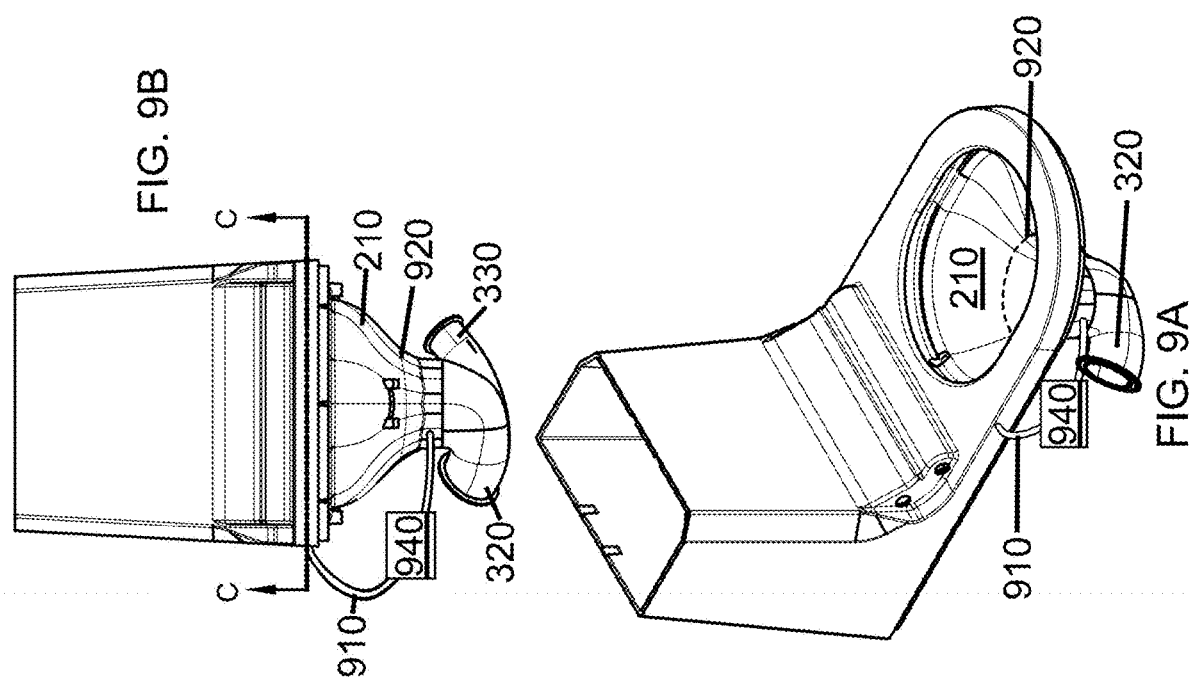

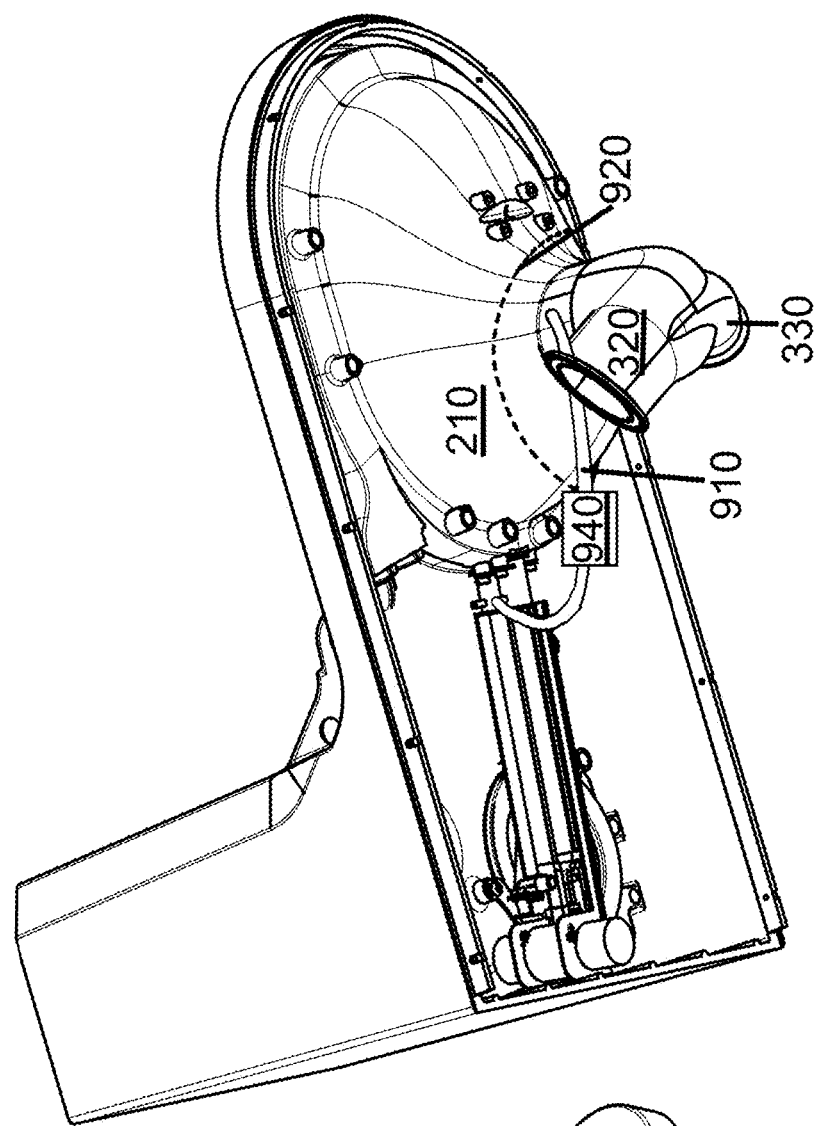
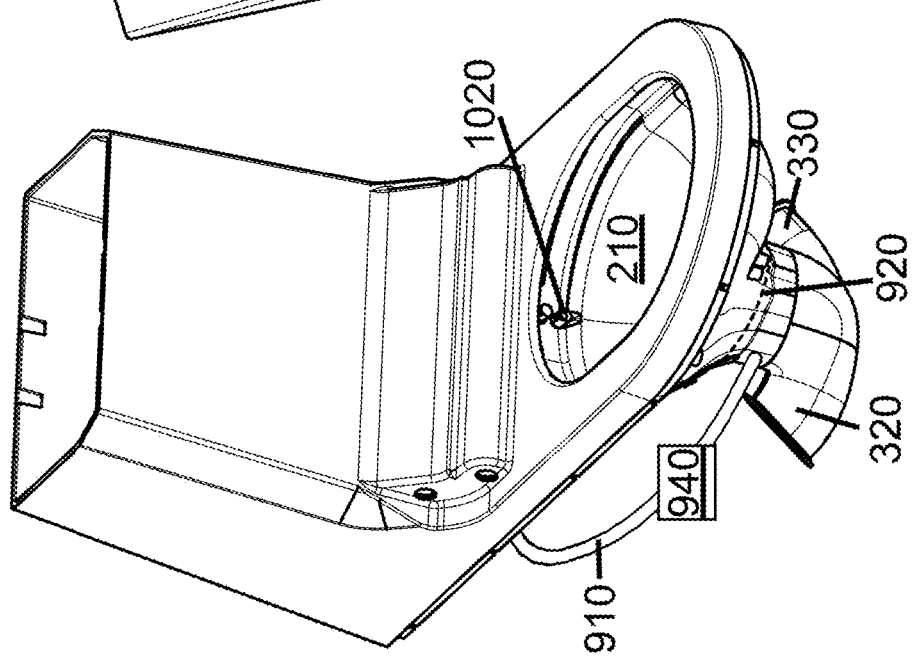
FIG. 10B
FIG. 10A

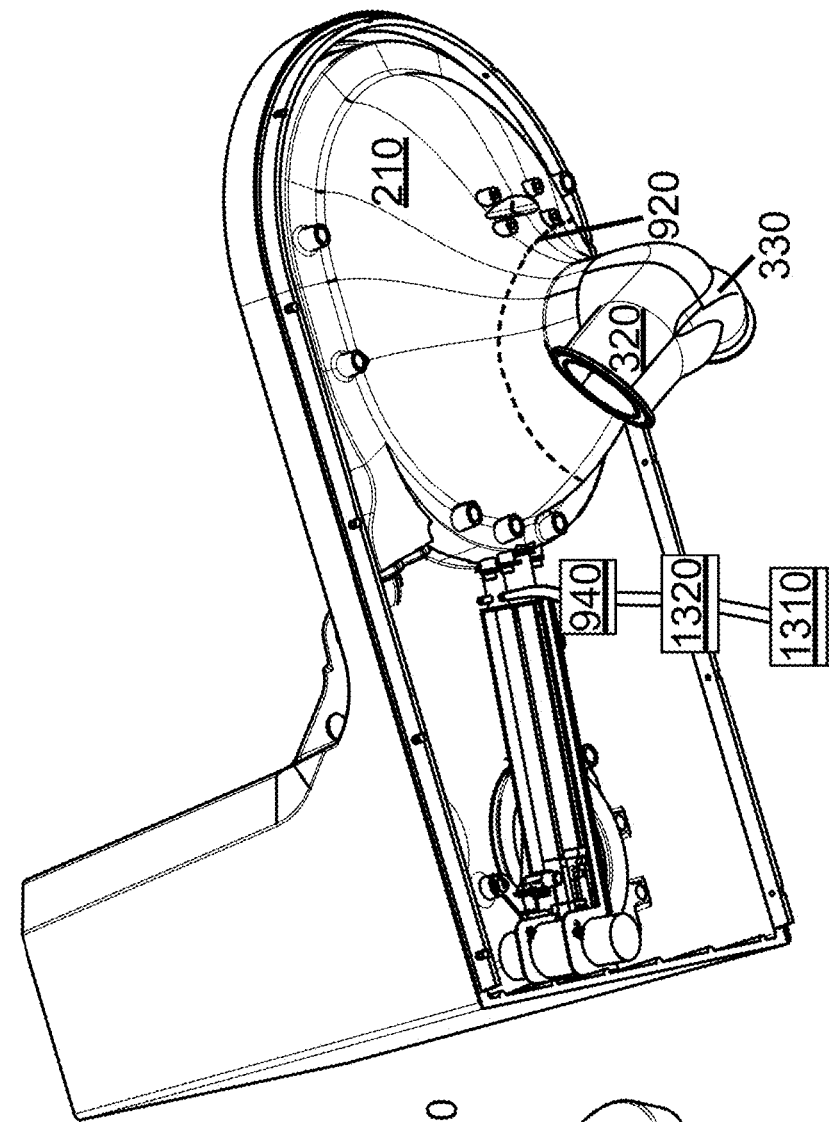
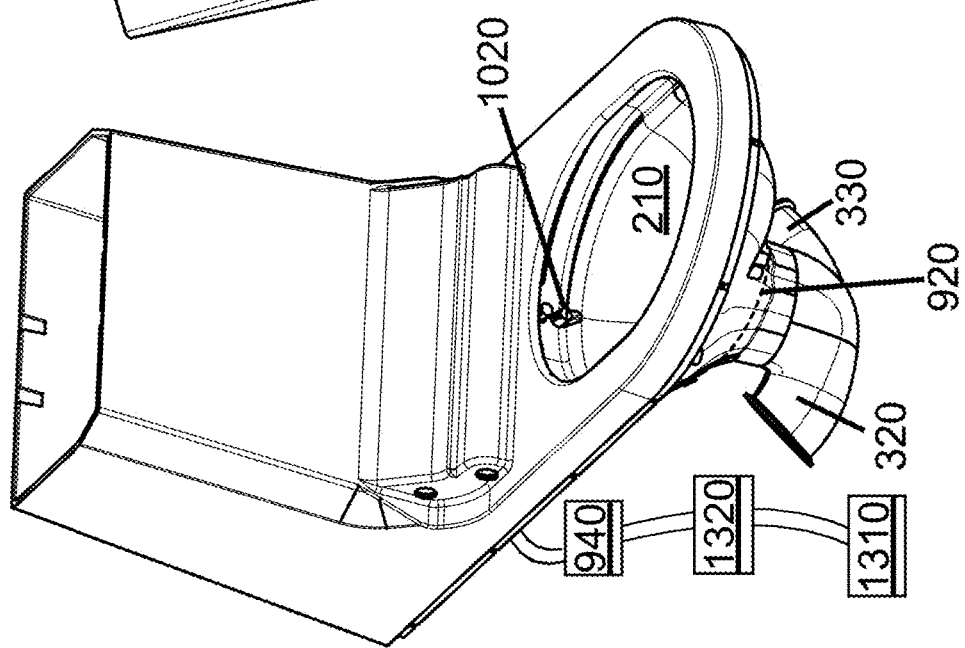
FIG. 13B
FIG. 13A

ANTIMICROBIAL TOILET WITH ELECTROLYZER

BACKGROUND

Field of the Invention

This disclosure relates to sanitization of toilet apparatuses and antimicrobial technology in toilets.

Background of the Invention

Toilets are used to deposit bodily waste which includes potentially infectious microbes. Multiple users may use a single toilet apparatus, particularly when the toilet is in a public location. Consequently, each user may be exposed to microbes from all users who have utilized the toilet since the toilet's last cleaning.

The greatest microbe load is typically located within the toilet bowl where user's deposit bodily waste. A typical western toilet includes toilet water where microbes may readily multiply. When a user flushes the toilet, the motion of the water may cause water droplets to be ejected out of the toilet bowl and onto a user or a toilet seat with which the next user may come in physical contact. Waste may also adhere to the sides of the toilet bowl above the water line creating a surface for microbes to remain between uses.

A toilet which continually disinfects as well as washes its toilet bowl would reduce user contact with potentially infectious microbes and may reduce the transmission of disease.

BRIEF SUMMARY OF THE INVENTION

We disclose an antimicrobial toilet which includes at least one electrolyzer, each including one or more pairs of electrodes. Each pair of electrodes includes an anode and a cathode each of which may be made of a conductive metal piece. In some embodiments, the cathode is manufactured at least in part from titanium metal and the anode is manufactured at least in part from iridium oxide-coated titanium. In some embodiments, electrodes may be conductive metal strips, conductive metal rings, or a combination of both conductive metal strips and conductive metal rings.

Each anode and each cathode may be connected by an electrical lead wire to an electrical power source. In some embodiments, the power source is a battery. The electrical lead wires may travel through holes in a part of the toilet, for example, the toilet bowl or the siphon tube, to connect electrodes inside the part with the electrical power source outside of the structure. A water tight seal may be positioned at each hole to prevent toilet water from leaking through the holes.

The toilet may include a toilet bowl and a siphon tube. The one or more pairs of electrodes may be positioned in the toilet bowl below the water line when the hydraulic circuit is in equilibrium. In other embodiments, the one or more pairs of electrodes are positioned within the siphon tube. In some embodiments, there may be pairs of electrodes in both the toilet bowl and the siphon tube. In these embodiments, the electrodes are submerged in water that is or has been in the toilet bowl and the water may include urine deposited therein by a user.

The electrodes in each pair may be near each other, for example separated by one inch or less, or separated by several inches, for example between approximately 1 inch and approximately 6 inches. In an example, an anode and a cathode may each be made of a conductive ring positioned within a siphon tube either near each other or separated by several inches as described above. In another example, an anode and a cathode may each be made of a conductive metal strip adhered to a side of the toilet bowl, either near each other or separate by several inches. In an example, the conductive metal strips may be positioned on opposite sides of the toilet bowl below the water line when the hydraulic circuit is in equilibrium.

In some embodiments, the pairs of electrodes may be positioned within one or more grooves in the toilet bowl or plumbing along the flush path. In an example, a single groove may extend from the circumference of the siphon tube. At least one electrode pair may be positioned within the groove. Toilet water may flow into the groove and be electrolyzed causing formation of antimicrobial reaction products which then flow out of the groove with the water. In other embodiments, multiple grooves may extend from the circumference of the siphon tube. A pair of electrodes may be positioned with each groove. Toilet water may flow in and out of each groove becoming electrolyzed along the way and resulting in water that includes the antimicrobial reaction products.

The submerged electrodes in each pair may pass an electric current between them which initiates at least one of two chemical reactions which require chloride ion or $Cl_2$. The reaction products possess antimicrobial properties capable of disinfection toilet surfaces in which they come in contact. The chloride required to drive the chemical reactions may be present in a standard fresh water source as may be provided to a typical home or building structure. However, urine contains more chloride than standard fresh water. Consequently, by actuating the electrodes when a user has urinated into the toilet, more reactants are available to drive the chemical reactions resulting in more reaction product.

Some embodiments of the toilet may include a pump and a water circulation conduit. The pump may be actuated and move electrolyzed water from the toilet bowl, through the water circulation conduit, and deliver it through one or more dispensers positioned above the water line. In an example, the one or more dispensers may be positioned to direct electrolyzed water toward the wall of the toilet bowl, the rim of the toilet bowl, a bidet system, or combinations thereof. In other examples, the water circulation conduit may deliver water from a fresh water which may not include urine as a source of chloride ions through an electrolyzer including one or more electrode pairs as described herein and through a dispenser positioned above the water line. Consequently, surfaces above the water line may be cleansed and disinfected with electrolyzed water.

In some embodiments, the pair of electrodes may be disposed within a fresh water conduit which transports fresh water from a fresh water source to the toilet tank. When a user flushes the toilet, electrolyzed water travels from the tank to the toilet bowl through a refill pipe and cleanses the sides of the toilet bowl with antimicrobial electrolyzed water.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings.

FIG. 2 is a perspective drawing of a siphon tube with a pair of circular electrodes according to an embodiment of the disclosure.

FIG. 9A is a perspective drawing of an aerial view of a toilet according to an embodiment of the disclosure which dispenses electrolyzed water at the rim of the toilet bowl.

FIG. 9B is a perspective drawing of a front view of the toilet of FIG. 9A.

FIG. 9C is a cross sectional view of the toilet of FIGS. 9A and 9B.

FIG. 10A is a perspective drawing of a toilet according to an embodiment of the disclosure which dispenses electrolyzed water into a bidet system.

FIG. 10B is a perspective drawing of the toilet of FIG. 10A as viewed from below the toilet.

FIG. 13A is a perspective drawing of a toilet according to the embodiment of the invention including an electrolyzer in contact with a fresh water source which cleanses bidet system.

FIG. 13B is perspective drawing of the toilet of FIG. 13A as seen from below the toilet bowl.

DETAILED DESCRIPTION OF THE INVENTION

Figure 1B:
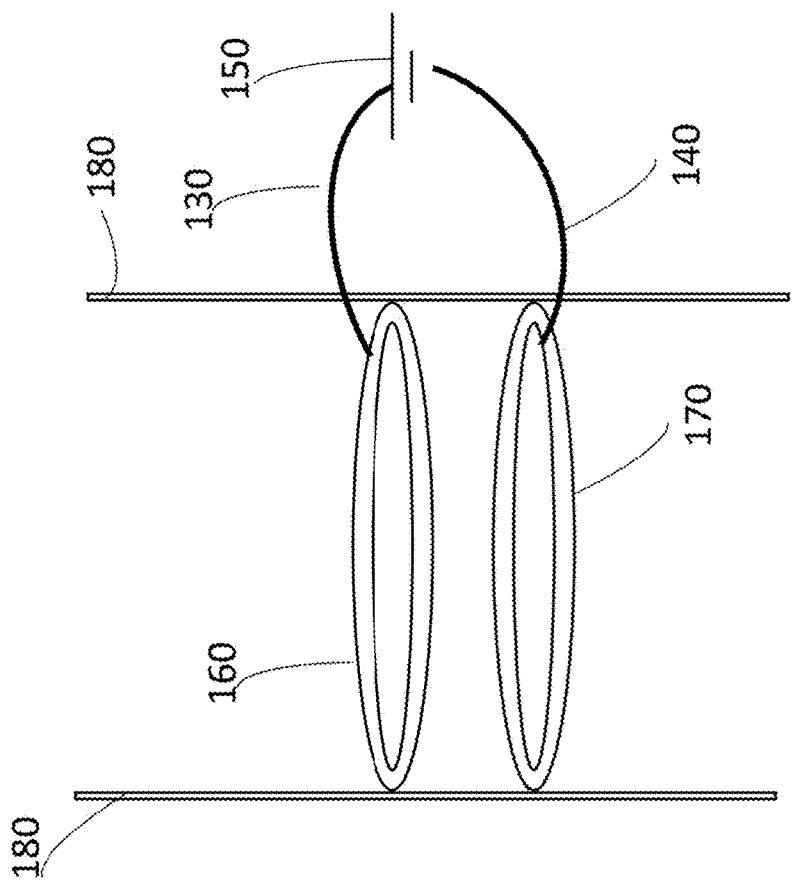
FIG. 1B is a schematic drawing of an embodiment of two circular electrodes according to an embodiment of the disclosure.

Definitions:

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "user" means the individual who comes in contact with the toilet disclosed herein and/or who deposits bodily waste into the toilet disclosed herein.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

We disclose an antimicrobial toilet which disinfects toilet water by electrolyzing the water in the hydraulic circuit. Sending an electric current through water that includes chloride ions releases chlorine into the liquid which then reacts with water to produce hypochlorous acid and hypochlorite ion in a pH-dependent manner. The following chemical reactions occur in water combined with chloride ions when electric current is passed through the water:

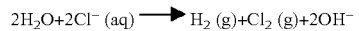

Urine may be the source of chloride ions which participate in the chemical reactions which occur in response to electrolysis. Chloride in human urine typically ranges from 25 to 40 mEq/L. Thus, by electrolyzing toilet water in the disclosed toilet after a user has urinated in the toilet bowl, hypochlorous acid and hypochlorite ions are produced, both of which have antimicrobial activity. Even after a flush, some urine and its chloride ions may remain in the toilet water which may be electrolyzed forming hypochlorous acid and hypochlorite ions. Consequently, the waste itself may be used to disinfect the toilet.

The disclosed antimicrobial toilet includes at least one pair of electrodes, each pair including an anode and a cathode. Some embodiments include multiple pairs of electrodes. The electrodes each include a conductive metal piece. In an example, the cathode comprises titanium metal and the anode comprises iridium oxide-coated titanium. In some examples, the electrodes are conductive metal strips. In other examples, the electrodes are circular and comprise conductive metal rings. The circular electrodes may be useful when positioning the electrodes against an inner diameter of a siphon tube or other toilet plumbing while the metal strips may be most useful when positioning the electrodes against the inner wall of the toilet bowl. The electrodes may be positioned in a location that is underwater when the hydraulic circuit is at equilibrium. In some embodiments the electrodes may be placed in a conduit which provides fresh water to the hydraulic circuit prior to the water entering the toilet bowl.

In some embodiments, the pairs of electrodes are disposed within one or more grooves. The grooves may comprise orifices within the inner wall of the toilet bowl, within the inner wall of the siphon tube, or anywhere along the flush path that is underwater when the hydraulic circuit is in equilibrium. In some embodiments, the grooves are extensions from the circular geometry of the siphon tube.

In some embodiments, both an anode and a cathode may be disposed within each groove. Toilet water may enter the groove between the anode and cathode. An electrical current may pass between the electrodes resulting in antimicrobial activity which disinfects the toilet water.

In embodiments in which the electrodes are placed within the toilet bowl, the anode and cathode of each pair may be placed near each other. For example, the anode may be between approximately 0.5 inches and approximately 6 inches from the cathode or approximately 1 inch from the cathode. In other embodiments, the anode may be on one side of the toilet bowl and the cathode may be on an opposite side of the toilet bowl. In these embodiments, the electrodes may be connected to the inner wall of the toilet bowl. In examples, there may be one, two, three, four, five, six, or more pairs of electrodes within the toilet bowl.

In embodiments in which the electrodes are positioned within the siphon tube, the anode and cathode of each pair may be placed near each other. For example, the anode may be between approximately 0.5 inches and approximately 6 inches from the cathode or, in an example, the anode may be approximately 1 inch from the cathode. There may be a single pair of electrodes within the siphon tube or multiple pairs of electrodes within the siphon tube. For example, there may be one, two, three, four, five, six, or more pairs of electrodes within the siphon tube. The electrodes may be connected to the inner surface of the siphon tube and may comprise metal strips or circular rings as described herein. Some embodiments may include electrodes constructed as both metal strips and as circular rings. Some embodiments of the toilet may include electrodes in both the toilet bowl and in the siphon tube. Some embodiments of the toilet may include electrodes within the water tight seal of the siphon tube.

Each electrode may be in electrical contact with an electrical lead wire. Each electrical lead wire may also be in contact with an electrical power source. Consequently, an electrical lead wire may conduct current between each electrode and an electrical power source. In some embodiments, the electrical power source is a battery although other sources of electrical power known in the art are within the scope of this disclosure.

In some embodiments, the antimicrobial toilet includes a pump and a water circulation conduit. The water circulation conduit may be in connection with the water in the hydraulic circuit and the pump may move the water through the water circulation conduit and out through one or more dispensers. Each dispenser may be an orifice, a nozzle, an atomizer, or other liquid dispenser known in the art. The one or more dispensers may direct water toward areas that are above the water line in the toilet to wash and disinfect these areas with electrolyzed water. For example, the one or more dispensers may disperse water from under a rim of the toilet bowl, from the inner wall of the toilet bowl above the water line, towards the bottom of a toilet seat, into a bidet system, or combinations thereof.

While some embodiments electrolyze water that has been in contact with urine which a user has deposited in the toilet bowl, other embodiments electrolyze water derived from a fresh water source which has no urine in it. Fresh water may have less chloride ions present in it relative to water that includes urine. However, water sources provided to most buildings, for example, through municipal water sources, contain enough chloride ions to participate in the electrolysis reaction.

In an example, the pair of electrodes and wires connecting them to a power source may be disposed within a fresh water conduit which is in fluid communication with a fresh water source and the toilet tank. Water may be electrolyzed as it passes through the fresh water conduit from the fresh water source and into the toilet tank after each flush. When the toilet is flushed, the electrolyzed water may travel through a refill pipe from the toilet tank into the toilet bowl. The walls of the toilet bowl may then be cleansed with electrolyzed antimicrobial water.

Figure 1A:
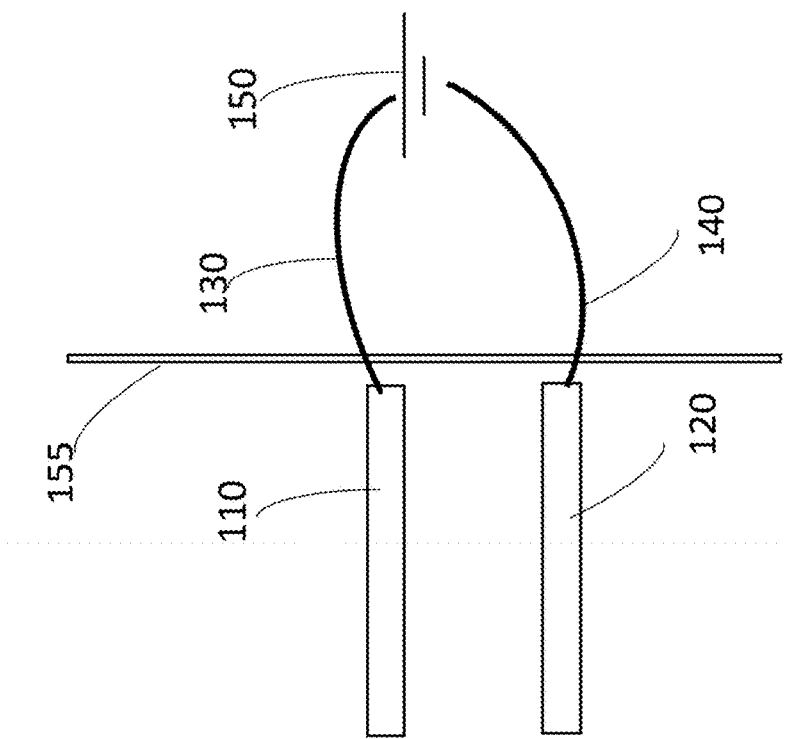
FIG. 1A is a schematic drawing of an embodiment of two strip electrodes according to an embodiment of the disclosure.

Referring now to the drawings, FIG. 1A illustrates an embodiment of a pair of electrodes comprising two strips of conductive metal. These strips include anode 110 and cathode 120. Electrical lead wires 130 and 140 connect anode 110 and cathode 120 respectively to power source 150. In this embodiment, power source 150 is depicted as a battery although other power sources are within the scope of the disclosure. Anode 110 and cathode 120 may be positioned in a variety of locations in the toilet, including, but not limited to, the toilet bowl, siphon tube, and the water input conduit as illustrated in other drawings provided herein. Electrical lead wires 130 and 140 are shown running through holes in wall 155. Wall 155 represents a structure within the flush circuit which may be, for example, the wall of the toilet bowl or the wall of the siphon tube. Anode 110 and cathode 120 are submerged in water and transmit an electric current through the water. The electric current initiates a chemical reaction that produces a product with antimicrobial activity. The product disinfects the toilet water and parts of the toilet coming in contact with the product. Seals as known in the art may be placed around the holes in wall 155 to prevent water leakage through the holes.

FIG. 1B is an alternative embodiment of the system shown in FIG. 1A. In FIG. 1B, the pair of electrodes includes two circular electrodes, anode 160 and cathode 170. Similar to the embodiment of FIG. 1A, FIG. 1B illustrates electrical lead wires 130 and 140 connecting anode 160 and cathode 170 to power source 150. Anode 160 and cathode 170 are placed within siphon tube 180. Electrical lead wires 130 and 140 run through holes in the wall of siphon tube 180 and connect anode 160 and cathode 170 to power source 150. Anode 160 and cathode 170 transmit electrical current through water in siphon tube 180 resulting in a product having antimicrobial activity which disinfects the toilet water and toilet parts coming in contact with the product. Seals as known in the art may be placed around the holes in siphon tube 180 to prevent water leakage through the holes.

FIG. 2 illustrates a partial view of a toilet according to an embodiment of the disclosure. The toilet includes toilet bowl 210 and flush tube 220. Anode 160 and cathode 170 make up a pair of circular electrodes positioned within siphon tube 220 as originally illustrated in FIG. 1B. Holes 230*a* and 230*b* are shown traversing the wall of siphon tube 220.

Electrical lead wires 240a and 240b pass through holes 230a and 230b, and connect anode 160 and cathode 170 to power source 250.

Figure 3:
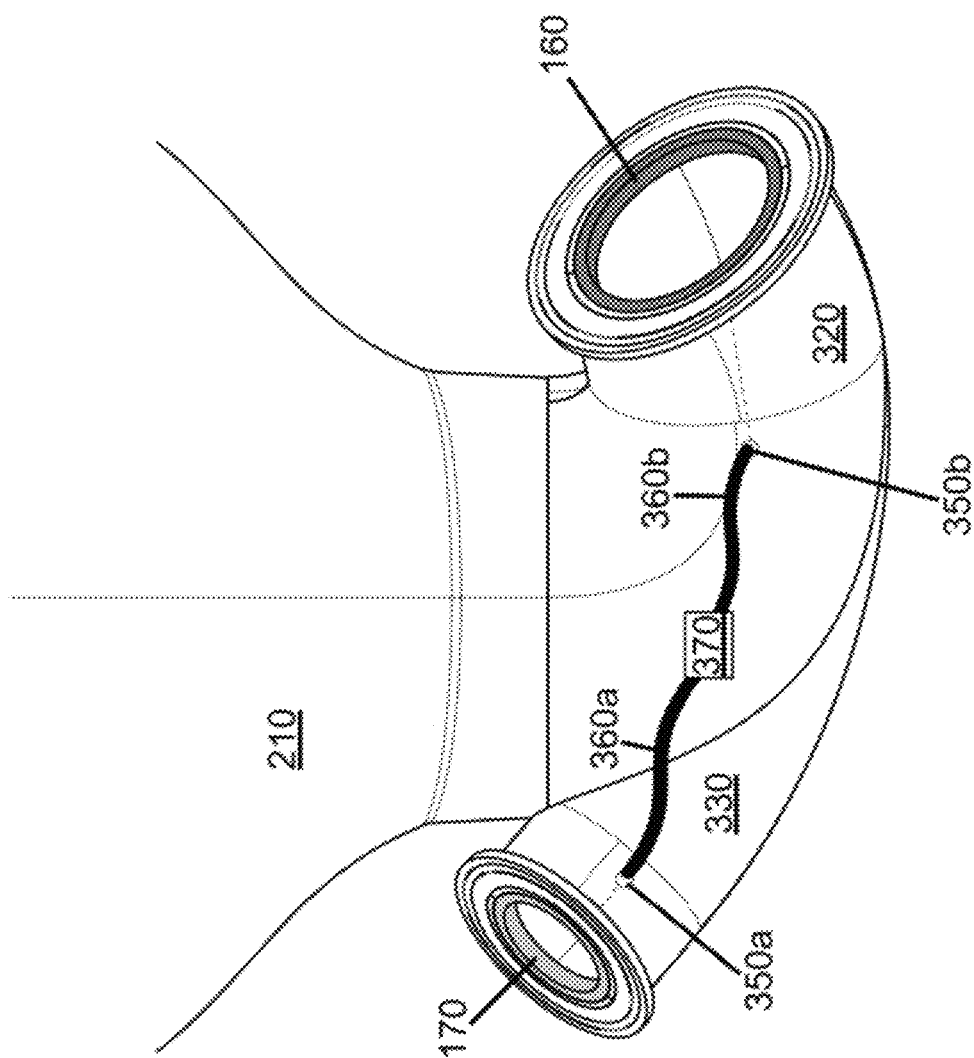
FIG. 3 is a perspective drawing of a siphon tube with a pair of circular electrodes, each in separate parts of the siphon tube, according to an embodiment of the disclosure.

FIG. 3 illustrates a partial view of a toilet according to another embodiment of the disclosure. The toilet includes toilet bowl 210, proximal siphon tube 320, and distal siphon tube 330. Proximal siphon tube 320 is nearest toilet bowl 210 and distal siphon tube 330 is nearer a sewer pipe. Proximal siphon tube 320 and distal siphon tube 330 are parts of the helical drain disclosed in U.S. Pat. No. 9,957,705 filed on May 31, 2016 although other siphon tube geometry is within the scope of this disclosure. Proximal siphon tube 320 includes a circular electrode, anode 160 within it. Distal siphon tube 330 includes a circular electrode, cathode 170 within it. In this embodiment, anode 160 and cathode 170 are separated by several inches of siphon tube. When actuated, an electric current passes through toilet water between anode 160 and cathode 170. Hole 350a bisects distal siphon tube 330. Electrical lead wire 360a passes through hole 350a and connects cathode 170 to power source 370. Likewise, hole 350b bisects proximal siphon 330. Electrical lead wire 360b passes through hole 350b and connects anode 160 to power source 370.

Figure 4:
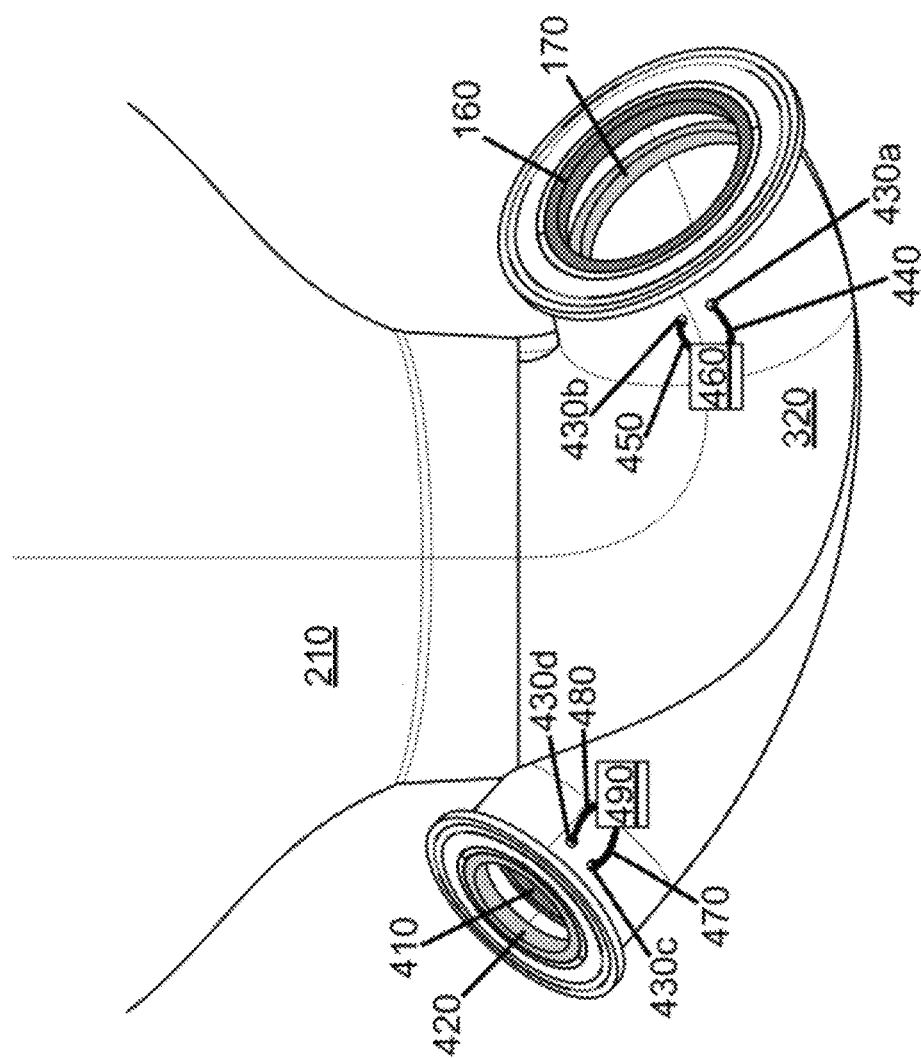
FIG. 4 is a perspective drawing of a siphon tube with two pairs of circular electrodes, each pair in separate parts of the siphon tube, according to an embodiment of the disclosure.

FIG. 4 illustrates a similar embodiment as that shown in FIG. 3. Like that of FIG. 3, the toilet of FIG. 4 includes toilet bowl 210, proximal siphon tube 320, and distal siphon tube 330. However, this embodiment includes multiple pairs of electrodes within the siphon tube geometry. Proximal siphon tube 320 has the circular electrode pair including anode 160 and cathode 170 inside it while distal siphon tube has the circular electrode pair including anode 410 and cathode 420 inside it. Holes 430a and 430b bisect proximal siphon tube 320. Electrical lead wire 440 passes through hole 430a and is in electrical connection with anode 160. Electrical lead wire 450 passes through hole 440b and is in electrical connection with cathode 170. Both electrical lead wires 440 and 450 are in electrical connection with power source 460. Consequently, anode 160 and cathode 170 are in electrical connection with power source 460 through electrical lead wires 440 and 450 respectively. Similarly, holes 430c and 430d bisect distal siphon tube 330. Electric lead wire 470 passes through hole 430c and is in electrical connection with anode 410. Electric lead wire 480 passes through hole 430d and is in electrical connection with cathode 420. Both electrical lead wires 460 and 470 are in electrical connection with power source 490. Consequently, anode 410 and cathode 420 a re in electrical connection with power source 490 through electrical lead wires 470 and 480 respectively.

Figure 5:
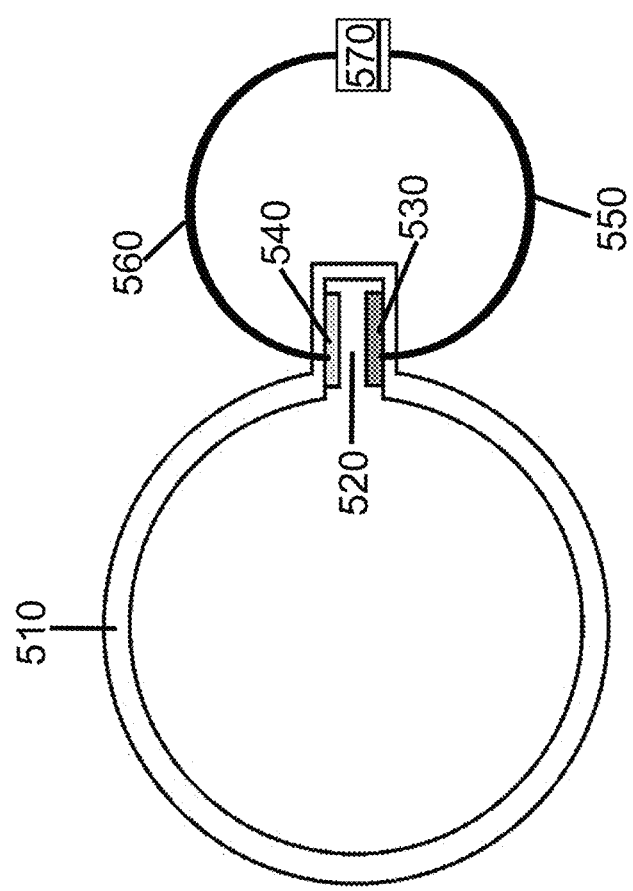
FIG. 5 is an orthogonal cross-sectional drawing of a siphon tube with electrodes in a single groove.

FIG. 5 illustrates a cross section of siphon tube 510. Groove 520 is an extension of the wall of siphon tube 510. An electrode pair is disposed within groove 520 which is made of two strips of conductive metal. The electrode pair includes anode 530 and cathode 540. Electrical lead wire 550 is in electrical connection with anode 530 while electrical lead wire 560 is in electrical connection with cathode 540. As shown in other drawings, the electrical lead wires pass through holes in the wall of groove 510. For purposes of clarity, the holes are not illustrated in FIG. 5. Seals as known in the art may be placed around the holes. Electrical lead wires 550 and 560 connect anode 530 and cathode 540 respectively to power source 570. Toilet water passing through siphon tube 510 may enter groove 520. An electric current passes through the toilet water between anode 530 and cathode 540 initiating a chemical reaction which produces a product that has antimicrobial activity. The product disinfects the toilet water and toilet parts with which it comes in contact.

Figure 6:
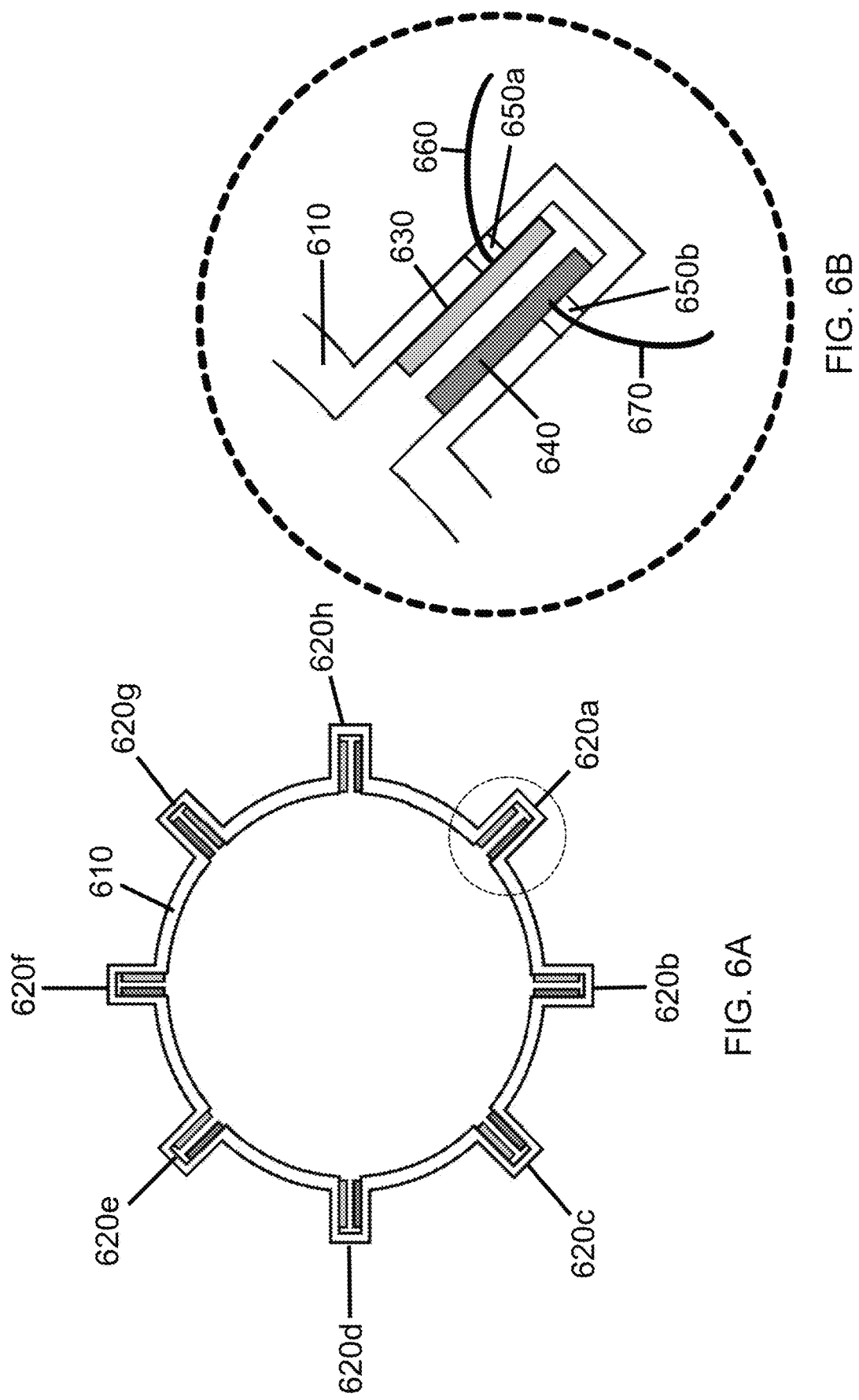
FIG. 6A is an orthogonal cross-sectional drawing of a siphon tube with electrodes in multiple grooves according to an embodiment of the disclosure.
FIG. 6B is an expanded view of a groove in the siphon tube of FIG. 6A.

FIG. 6A illustrates a cross section of siphon tube 610. The embodiment of FIG. 6 resembles that of FIG. 5. However, instead of a single groove as shown in siphon tube 510, siphon tube 610 includes 8 grooves extending from its wall. These include grooves 620a-h. Each of grooves 620a-h include a pair of electrodes comprising conductive metal strips.

FIG. 6B is a blown-up view of groove 620a shown in FIG. 6A. An electrode pair is disposed within groove 620a which is made of two strips of conductive metal. The electrode pair includes anode 640 and cathode 630. Holes 650a and 650b bisect the wall of groove 620b. Electrical lead wire 660 is in electrical connection with cathode 630 and passes through hole 650a while electrical lead wire 670 is in electrical connection with anode 640 and passes through hole 650b. Both electrical lead wires 660 and 670 connect to a power source, the latter of which is not shown for purposes of clarity. Grooves 620b-h are as illustrated in FIG. 6B.

Figure 7:
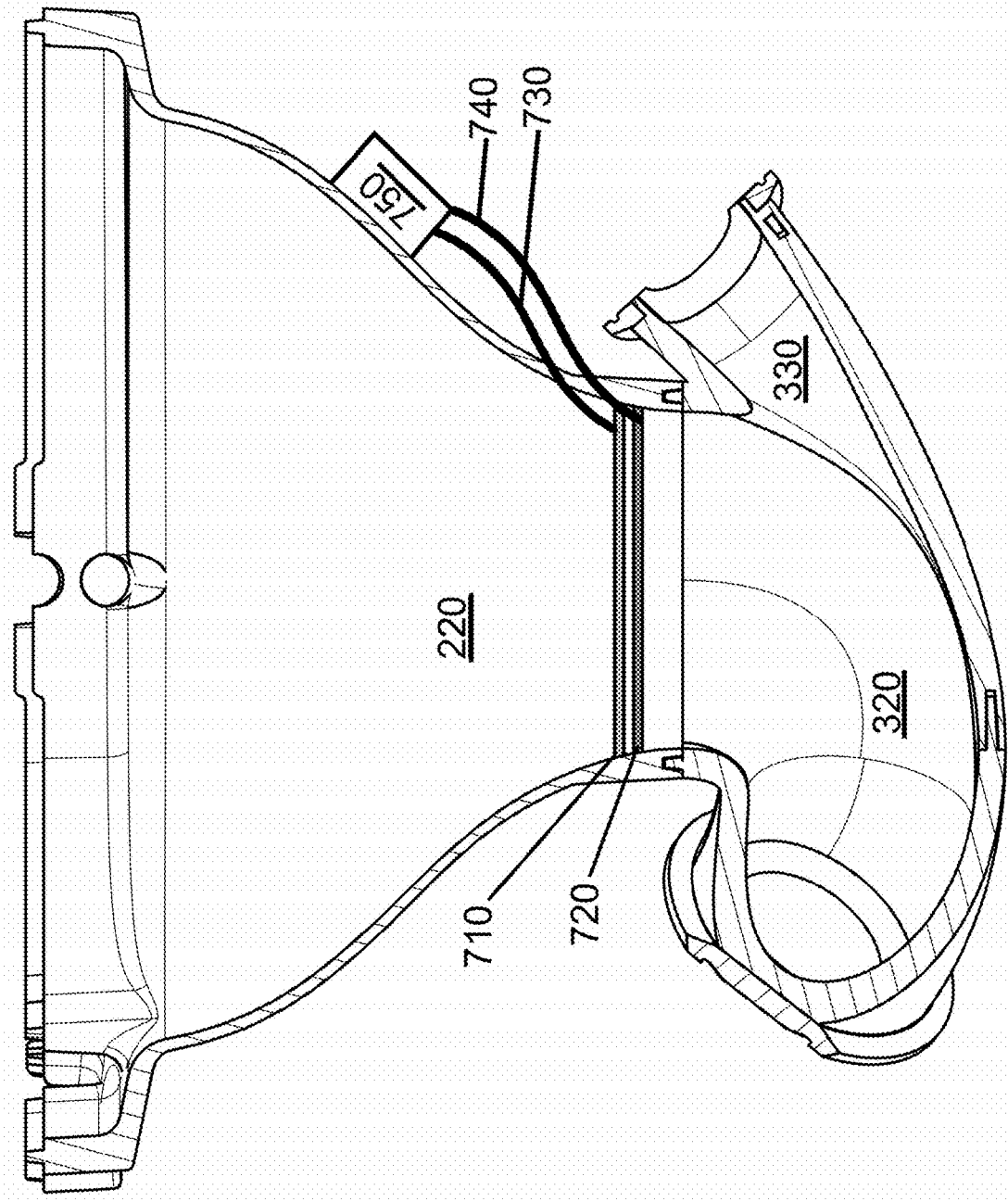
FIG. 7 is a cross-sectional view of a toilet that includes strip electrodes in the toilet bowl according to an embodiment of the disclosure.

FIG. 7 is a cross sectional view of another embodiment of the disclosed toilet which includes toilet bowl 220, proximal siphon tube 320 and distal siphon tube 330. The siphon tube geometry is as initially illustrated in FIG. 3. Two electrodes, cathode 710 and anode 720 are constructed of conductive metal strips and adhered to the inner wall of toilet bowl 220. Cathode 710 and anode 720 are positioned in toilet bowl 220 at a point which is below the water line when the hydraulic circuit of the toilet is at equilibrium. Electrical lead wires 730 and 740 extend from cathode 710 and anode 720 respectively to power source 750. Each of electrical lead wires 730 and 740 pass through a hole in the wall of toilet bowl 220 which is not shown for purposes of clarity. A water tight seal as known in the art may be placed around each hole to prevent water leakage.

Figure 8:
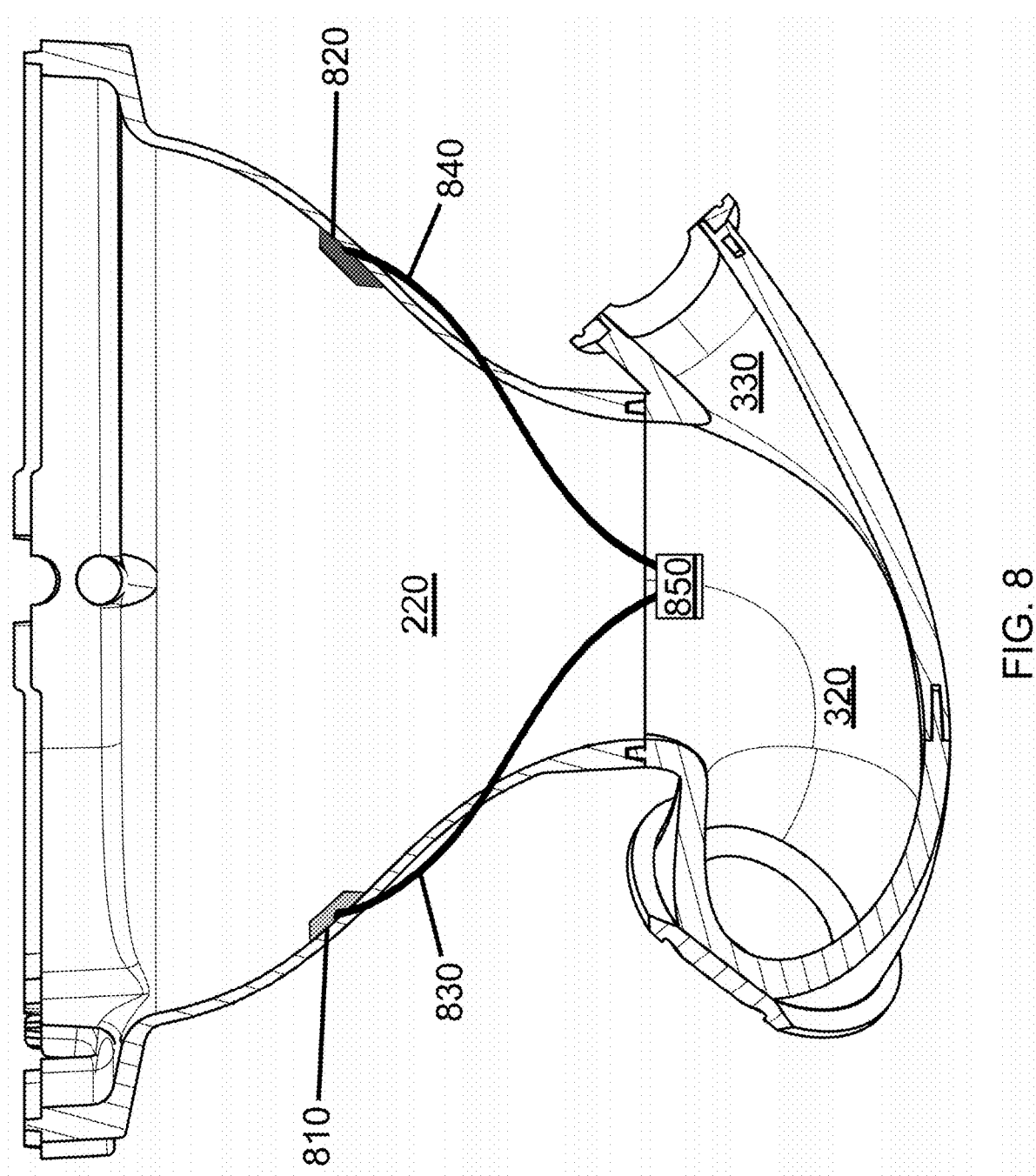
FIG. 8 is a cross-sectional view of a toilet that includes strip electrodes on opposite sides of the toilet bowl according to an embodiment of the disclosure.

FIG. 8 is a cross sectional view of another embodiment of the disclosed toilet which is similar to that shown in FIG. 7. A relevant difference is that the embodiment shown in FIG. 8 includes cathode 810 on the inner wall of toilet bowl 220 on one side and anode 820 which is on the inner wall of toilet bowl 220 on the opposite side. This is in contrast with cathode 710 and anode 720 shown in FIG. 7 which are side-by-side with a small space, for example, 1 inch, between them. Electrical lead wires 830 and 840 connect cathode 810 and anode 820 respectively to power source 850. Electrical lead wires 830 and 840 pass through holes in toilet bowl 220 which include water tight seals to prevent water leakage. The holes and seals are not shown for purposes of clarity.

FIG. 9A illustrates toilet according to an embodiment of an invention which includes water circulation conduit 910 which is in fluid connection with the toilet water in toilet bowl 210. The toilet includes any of the embodiments of the electrolyzers that are within the scope of the disclosure and which result in electrolyzed water in the toilet bowl. The lower end of water circulation conduit 910 inserts in to toilet bowl 210 at a point that is below water line 920. Pump 940 moves water from toilet bowl 210 and upward through water circulation conduit 910.

FIG. 9B is a view from directly in front of the toilet of FIG. 9A. This view clarifies the lower point of water circulation conduit 910 entering toilet bowl 210 at a point that is below water line 920.

FIG. 9C illustrates a cross-sectional view of the toilet of FIG. 9B taken through the plane marked as A in FIG. 9B. FIG. 9C illustrates orifice 930 which is in fluid contact with the upper end of water circulation conduit 910. Consequently, pump 940 moves water from toilet bowl 210 through water circulation conduit 910 and dispenses it through orifice 930 which directs the water upward into the rim of toilet bowl 210. The electrolyzed water from toilet bowl 910 dispensed through orifice 930 washes the rim of toilet bowl 210. In some embodiments, multiple dispensers may be present and direct electrolyzed water toward the rim of toilet bowl 210 all along the circumference of the rim.

FIG. 10A illustrates a toilet according to an embodiment of the disclosure which, similar to the toilet of FIGS. 9A and 9B, dispenses electrolyzed water from the toilet bowl to wash and disinfect other parts of the toilet. The toilet includes any of the embodiments of the electrolyzers that are within the scope of the disclosure and which result in electrolyzed water in the toilet bowl. In this embodiment, water circulation conduit 910 is in fluid communication with water in toilet bowl 210 and bidet nozzle 1020. Pump 940 moves electrolyzed water from toilet bowl 210, through water circulation conduit 910 and dispenses the electrolyzed water through bidet nozzle 1020.

FIG. 10B is a view of the toilet of FIG. 10A from below which illustrates water circulation conduit 910 as it enters the bidet system to dispense electrolyzed water through bidet nozzle 1020. In doing so, the electrolyzed water washes and disinfects the bidet system including bidet nozzle 1020.

Figure 11B:
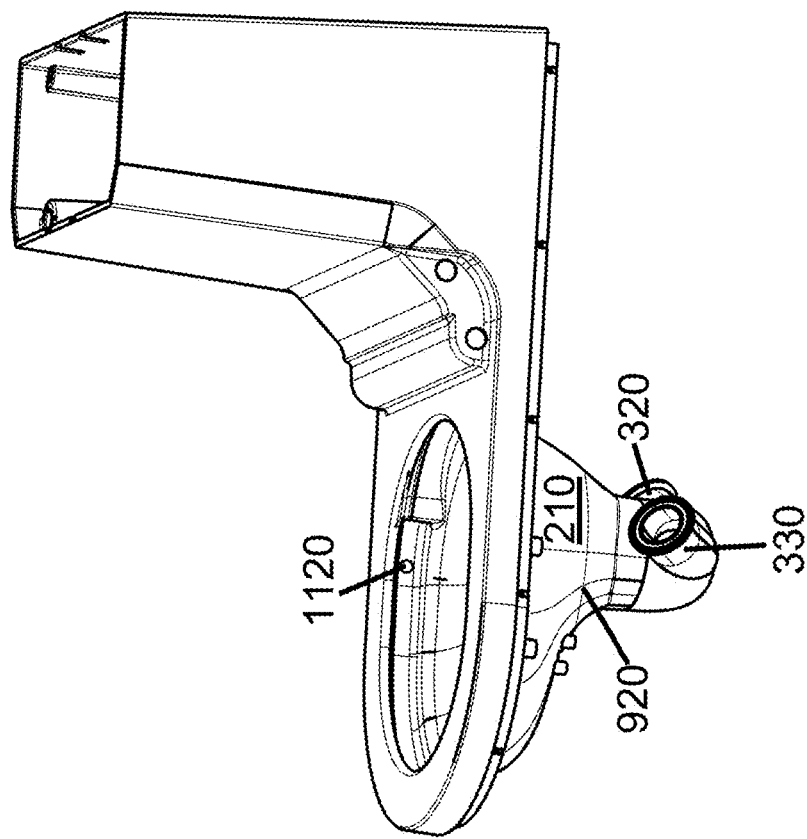
FIG. 11B is a perspective drawing of the toilet of FIG. 11A turned 90 degrees.
Figure 11A:
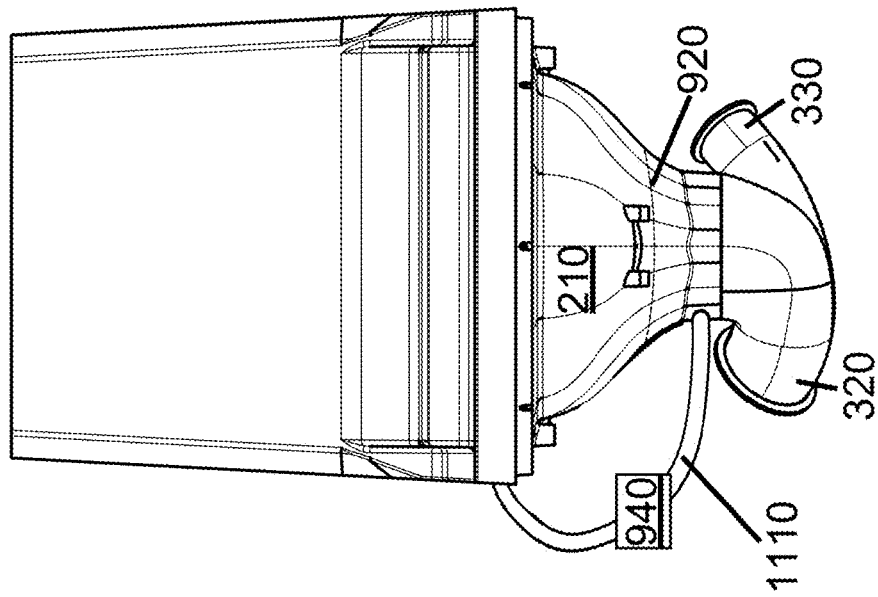
FIG. 11A is a perspective drawing of a toilet according to an embodiment of the disclosure which dispenses electrolyzed water through the toilet bowl wall above the water line.

FIG. 11A also illustrates a toilet according to an embodiment of the disclosure which, similar to the toilet of FIGS. 9A-9C, 10A, and 10B, dispenses electrolyzed water from the toilet bowl to wash and disinfect other parts of the toilet. The toilet includes any of the embodiments of the electrolyzers that are within the scope of the disclosure and which result in electrolyzed water in the toilet bowl. The toilet of FIG. 11A differs from that of FIGS. 9A-9C in that it dispenses the electrolyzed water outward from the wall of toilet bowl 210 through orifice 1120 instead of into the rim as shown in FIGS. 9A-C. Pump 940 moves electrolyzed water from toilet bowl 210, through water circulation conduit 910 and dispenses the electrolyzed water through orifice 1120. FIG. 11B is a side view of the toilet of FIG. 11A and shows orifice 1120. Orifice 11B is located in the wall of toilet bowl 210 above water line 920. The water dispensed from orifice 1120 cleanses and disinfects the wall of toilet bowl 210 with electrolyzed water.

Figure 12B:
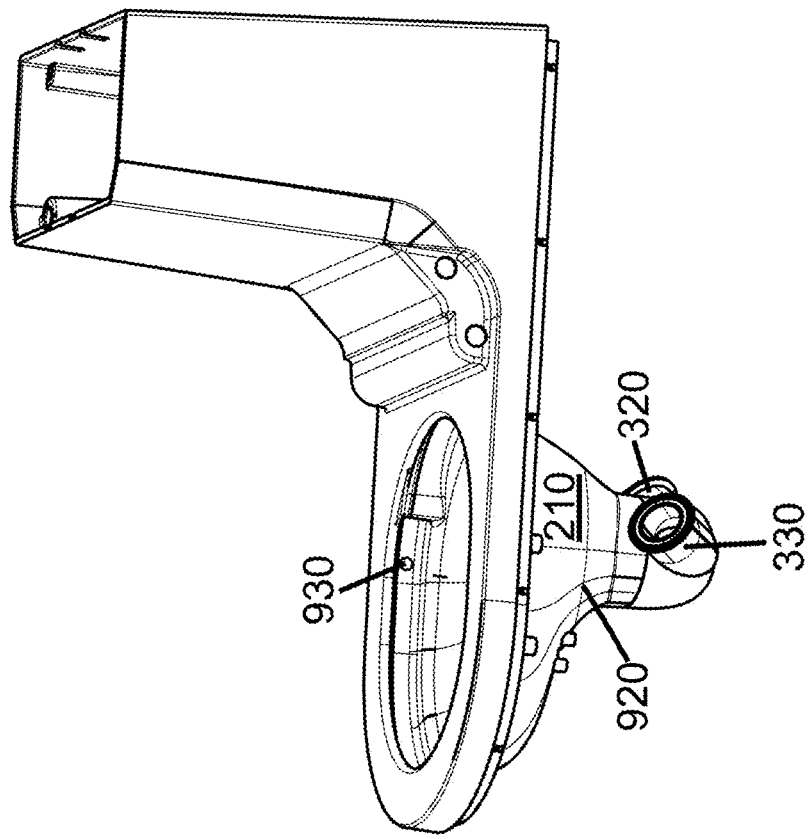
FIG. 12B is a perspective drawing of the toilet of FIG. 12A turned 90 degrees.
Figure 12A:
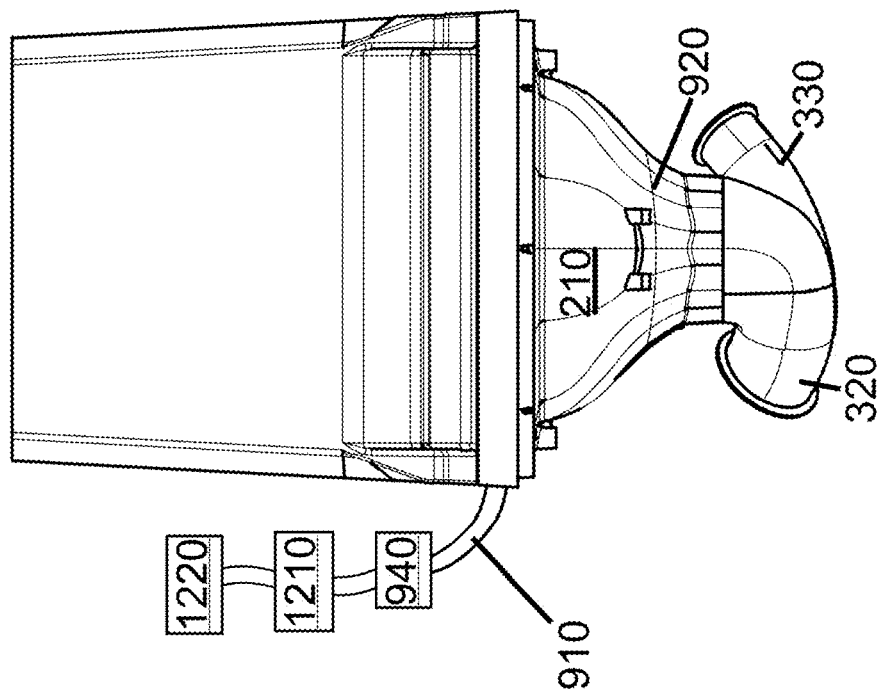
FIG. 12A is a perspective drawing of a toilet according to the embodiment of the invention including an electrolyzer in contact with a fresh water source.

FIG. 12A illustrates toilet according to an embodiment of an invention which includes water circulation conduit 910 which is in fluid connection with the toilet water in toilet bowl 210 and with fresh water source 1220. Water from fresh water source 1220 passes through water circulation conduit 910 then through electrolyzer 1210. Pump 940 provides the force to move the water through water circulation conduit 910. The electrolyzed water enters toilet bowl 210 through orifice 1120 at the rim of toilet bowl 210. Orifice 1120 is originally shown in the embodiment of FIG. 11B. In this embodiment, the electrolyzed water used chloride ions that are already in the fresh water source and not provided by urine.

FIG. 12B is a side view of the toilet illustrated in FIG. 12A which illustrates orifice 1120 at the rim of toilet bowl 210.

FIG. 13A illustrates a toilet according to an embodiment of the disclosure which includes water circulation conduit 910 which is in fluid connection with the toilet water in toilet bowl 210 and with fresh water source 1310. Water from fresh water source 1310 passes through water circulation conduit 910 then through electrolyzer 1320. Pump 940 provides the force to move the water through water circulation conduit 910. The electrolyzed water enters toilet bowl 210 through bidet nozzle 1020 originally presented in FIG. 10B. In doing so, the electrolyzed water which has not come in contact with urine washes and disinfects the bidet system including bidet nozzle 1020.

FIG. 13B is a view of the toilet of FIG. 13A from below which illustrates water circulation conduit 910 as it enters the bidet system to dispense electrolyzed water through bidet nozzle 1020.

Figure 14:
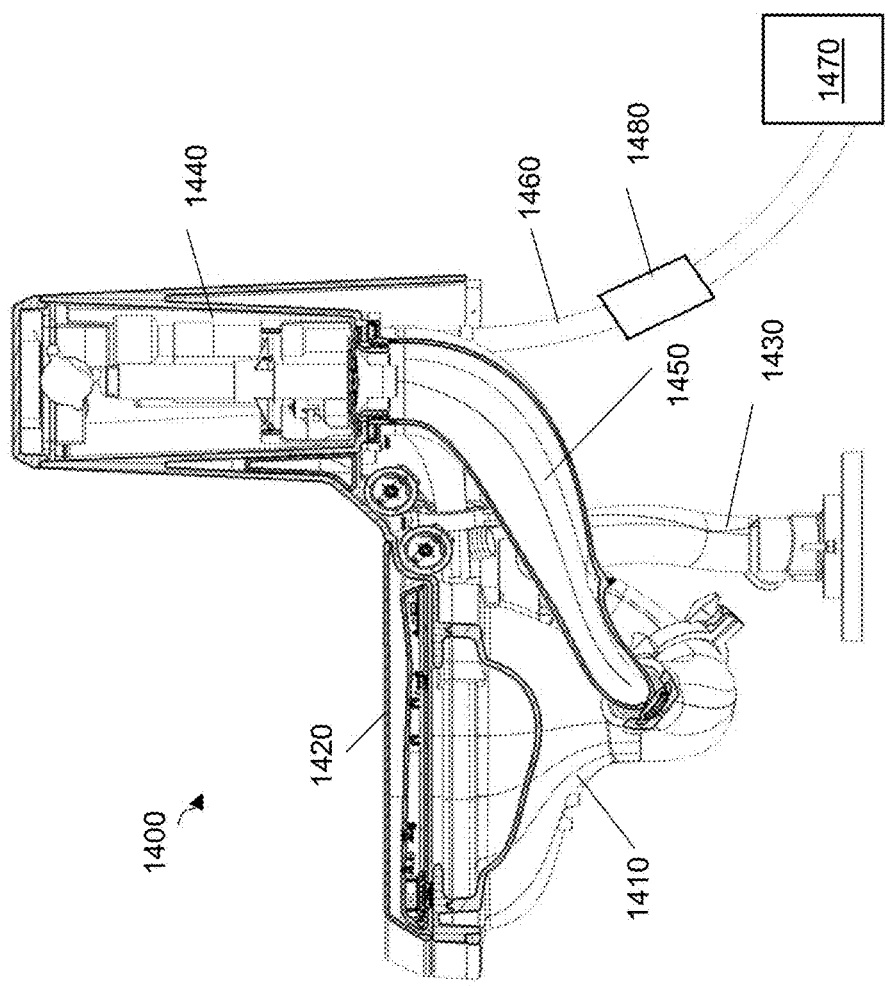
FIG. 14 is a cross-sectional view of a toilet in which the electrolyzer is between a fresh water source and the toilet tank.

FIG. 14 is a cross-sectional view of toilet 1400 which illustrates an embodiment of the disclosure in which the electrolyzer is disposed within a conduit which provides fresh water to toilet 1400. Like a traditional water toilet, toilet 1400 includes toilet bowl 1410 and toilet seat 1420. Waste and water from toilet bowl 1410 may travel through siphon pipe 1430 into a sewer pipe. Toilet 1400 also includes tank 1440 which may be filled with fresh water. The fresh water from tank 1440 may move through refill pipe 1450 into toilet bowl 1410 when a user flushes toilet 1400 to refill toilet bowl 1410 with fresh water. Fresh water conduit 1460 is in fluid connection with tank 1440 and fresh water source 1470. After a flush event, fresh water from fresh water source 1470 travels through fresh water conduit 1460 to replace the water in tank 1440. Electrolyzer 1480 is disposed within fresh water conduit 1460 and electrolyzes the fresh water as it travels through fresh water conduit 1460. Thus, tank 1440 houses electrolyzed water. When toilet 1400 is subsequently flushed, water which includes the chemical described herein which has antimicrobial activity may enter toilet bowl 1410 and cleanse the walls of toilet bowl 1410. Electrolyzer 1480 may be structured according to any of the embodiments disclosed herein. In an example, electrolyzer 1480 may be structures according to the embodiment in FIG. 1B of the instant application.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. An antimicrobial toilet, comprising:
   a hydraulic circuit comprising a siphon tube and a fresh water conduit, wherein the fresh water conduit is in fluid communication with the siphon tube and a source of fresh water;
   a toilet bowl;
   at least one pair of electrodes, wherein each of the at least one pair of electrodes comprises a cathode and an anode, and wherein each of the at least one pair of electrodes is positioned within the hydraulic circuit;
   an electrical power source; and
   at least two electrical lead wires, wherein each of the at least two electrical lead wires are in contact with either the anode or the cathode of each of the at least one pair of electrodes and with the electrical power source;

wherein at least one of the at least one pair of electrodes comprises two conductive rings disposed within the siphon tube.

2. The antimicrobial toilet of claim 1, wherein the electrical power source comprises a battery.

3. The antimicrobial toilet of claim 1, wherein the at least one pair of electrodes is positioned in a location that is submerged in water when the hydraulic circuit is at equilibrium.

4. The antimicrobial toilet of claim 1, wherein the anode and the cathode in at least one of the at least one pair of electrodes are positioned at opposite sides of the toilet bowl.

5. The antimicrobial toilet of claim 1, wherein at least one of the at least one pair of electrodes comprises two conductive metal strips.

6. The antimicrobial toilet of claim 5, wherein the conductive metal strips are positioned within the toilet bowl.

7. The antimicrobial toilet of claim 5, wherein the at least one pair of electrodes comprises a plurality of conductive metal strips.

8. The antimicrobial toilet of claim 1, wherein the two conductive rings are positioned within a water seal within the siphon tube.

9. The antimicrobial toilet of claim 1, wherein the at least one pair of electrodes comprises a plurality of pairs of electrodes, each of the plurality of pairs of electrodes comprising two conductive rings.

10. The antimicrobial toilet of claim 1, wherein at least one of the at least one pair of electrodes is disposed within a groove, wherein the groove is disposed along the flush path.

11. The antimicrobial toilet of claim 1, wherein the cathode comprises titanium metal and the anode comprises iridium oxide-coated titanium.

12. The antimicrobial toilet of claim 1, wherein the pairs of electrodes are configured to perform one or both of the following chemical reactions in toilet water combined with urine:

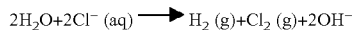

13. The antimicrobial toilet of claim 1, wherein the at least one pair of electrodes and the at least two electrical lead wires are disposed within the fresh water conduit.

14. An antimicrobial toilet, comprising:
a hydraulic circuit comprising a siphon tube and a fresh water conduit, wherein the fresh water conduit is in fluid communication with the siphon tube and a source of fresh water;
a toilet bowl;
at least one pair of electrodes, wherein each of the at least one pair of electrodes comprises a cathode and an anode, and wherein each of the at least one pair of electrodes is positioned within the hydraulic circuit;
an electrical power source; and
at least two electrical lead wires, wherein each of the at least two electrical lead wires are in contact with either the anode or the cathode of each of the at least one pair of electrodes and with the electrical power source;
a pump;
a water circulation conduit; and
at least one dispenser, wherein the at least one dispenser is located above a level of water in the bowl when the hydraulic circuit is in equilibrium; and wherein the pump is configured to move electrolyzed water from the toilet bowl, through the water circulation conduit, and through the at least one dispenser back into the toilet bowl.

15. The antimicrobial toilet of claim 14, wherein at least one of the at least one dispenser is in fluid communication with a bidet system.

16. The antimicrobial toilet of claim 14, wherein at least one of the at least one dispenser is configured to direct electrolyzed water under a rim of the toilet bowl.

17. The antimicrobial toilet of claim 16, wherein the at least one dispenser comprises a plurality of dispensers each configured to direct electrolyzed water under the rim of the toilet bowl.

18. The antimicrobial toilet of claim 14, wherein at least one of the at least one dispenser is configured to direct electrolyzed water toward a wall of the toilet bowl.

* * * * *